United States Patent
Yeh et al.

(10) Patent No.: US 9,101,672 B2
(45) Date of Patent: Aug. 11, 2015

(54) USE OF GOLD NANOCLUSTERS IN AMELIORATING OXIDATE STRESS AND/OR AGING

(75) Inventors: Hung-I Yeh, Taipei (TW); Walter H. Chang, Zhongli (TW); Cheng-An Lin, Zhongli (TW); Hsueh-Hsiao Wang, Taipei (TW)

(73) Assignees: MACKAY MEMORIAL HOSPITAL (TW); CHUNG YUAN CHRISTIAN UNIVERSITY (TW)

( * ) Notice: Subject to any disclaimer, the term of this patent is extended or adjusted under 35 U.S.C. 154(b) by 899 days.

(21) Appl. No.: 13/218,625

(22) Filed: Aug. 26, 2011

(65) Prior Publication Data

US 2013/0052270 A1 Feb. 28, 2013

(51) Int. Cl.
*A61K 47/48* (2006.01)
*A61K 9/51* (2006.01)
*B82Y 5/00* (2011.01)

(52) U.S. Cl.
CPC ......... *A61K 47/48861* (2013.01); *A61K 9/5123* (2013.01); *B82Y 5/00* (2013.01)

(58) Field of Classification Search
CPC ... B82Y 5/00; A61K 33/24; A61K 47/48861; A61K 47/48884
See application file for complete search history.

(56) References Cited

U.S. PATENT DOCUMENTS

2011/0250132 A1* 10/2011 Seetharama ................. 424/1.65

FOREIGN PATENT DOCUMENTS

JP 2008156440 * 7/2007

OTHER PUBLICATIONS

Garcia et al. (Chem Commun, 2005 369-371).*
Kagan et al. (Biochemcial Pharmacology 1992, 44(8) 1637-1649).*
Reuter et al. (Free Radic Biol Med 2010, 49 (11), 1603-1616).*
Liu et al. (J. Agric. Food Chem. 2005, 53, 4311-4314).*
Lin, C.A. et al. "Synthesis, Characterization, and Bioconjugation of Fluorescent Gold Nanoclusters Toward Biological Labeling Applications", ACS Nano. 3, 395-401.
Jana et al. "Single-phase and gram-scale routes toward nearly monodisperse Au and other noble metal nanocrystals" J Am Chem Soc 125 (47): 14280-1 (2003) PMID 14624568.
Kenneth B. Beckman and Bruce N. Ames. "The Free Radical Theory of Aging Matures" Physiological Reviews, vol. 78, No. 2, Apr. 1998, pp. 547-582.

* cited by examiner

*Primary Examiner* — Abigail Fisher
*Assistant Examiner* — Jessica Kassa
(74) *Attorney, Agent, or Firm* — Thomas Horstemeyer, LLP

(57) ABSTRACT

Disclosed herein is the novel use of a gold nanocluser for ameliorating oxidative stress and/or aging of a cultured cell or a subject having an oxidative stress and/or aging condition mediated by a vascular factor. The gold nanocluster has a particle size ranging from about 0.1 to 20 nm, and preferably is dihydrolipoic acid (DHLA) coated gold nanocluster.

2 Claims, 1 Drawing Sheet

USE OF GOLD NANOCLUSTERS IN AMELIORATING OXIDATE STRESS AND/OR AGING

BACKGROUND OF THE INVENTION

1. Field of the Invention

The present disclosure relates to the use of gold nanoclusters; particularly, the novel use of red-emitting gold nanoclusters in ameliorating oxidative stress and/or aging.

2. Description of Related Art

Previous studies suggest that aging process and various disease-related degenerative processes are caused, at least, partly by the free-radical oxidative stress and/or the oxidative shift in the thio/disulfide redox state (Beckeamen and Ames, Physiol. Rev. 1998 78:547-581). Oxidative stress has also been implicated as resulted from factors such as inflammation or a vascular disease. Therefore, there exists in this art a need to find an agent which ameliorates the oxidative stress in the context of aging and various disease conditions including vascular diseases. Accordingly, agent that ameliorates oxidative stress and, thus, aging process, would be a potential candidate for the development of a medicament or pharmaceutical composition for treating such diseases.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

The present invention is based on the unexpected discovery that red-emitting gold nanoclusters are effective in ameliorating oxidative stress and/or aging of a cultured cell, hence are useful as an agent to suppress or inhibit cellular senescence, as well as for future development of a medicament for ameliorating oxidative stress and/or aging mediated by a vascular factor such as inflammation, or a vascular disease.

In one aspect, the present disclosure is directed to a method of ameliorating oxidative stress and/or aging of a cultured cell. The method includes contacting the cultured cell with an effective amount of a gold nanocluster having a particle size ranging from 0.1 to 20 nm.

In one example, the gold nanocluster is dihydrolipoic acid (DHLA) coated gold nanocluster. The cultured cell is selected from the group consisting of human arotic endothelial cell (HAEC), human endothelial progenitor cell (HEPC), human epithelial cells, human embryonic stem cell, and human mesenchymal stem cell. The amount of gold nanoclusters contacting the cultured cells is about 1 to 1,000 nM.

In another aspect, the present disclosure is directed to a use of the gold nanocluster described above for manufacturing an agent for ameliorating oxidative stress and/or aging of a cultured cell.

Also within the scope of the present disclosure is a pharmaceutical composition for treating an oxidative stress and/or aging condition of a subject. The pharmaceutical composition includes an effective amount of the gold nanocluster described above and a pharmaceutically acceptable excipient. The subject is a human or an animal, preferably a mammal.

Further within the scope of the present disclosure is a method for treating an oxidative stress and/or aging condition of a subject. The method includes administering to the subject the pharmaceutical composition of the present invention to ameliorating oxidative stress and/or aging of the subject. The oxidative stress and/or aging condition of the subject is mediated by a vascular factor such as inflammation or a vascular disease. The vascular disease is any of atherosclerosis, coronary artery disease (CAD), myocardial infraction (MI), ischemia, stroke, peripheral vascular disease, or pulmonary vascular disease. The subject is a human or an animal, preferably a mammal.

The details of many embodiments of the invention are set forth in the detailed description and the claims below. Other features, objects, and advantages of the invention will become better understood with reference to the following detailed description and the appended claims.

BRIEF DESCRIPTION OF THE DRAWINGS

These and other features, aspects and advantages of the present invention will become better understood with reference to the following description, appended claims and the accompanying drawings, where:

DESCRIPTION

Figure 1:
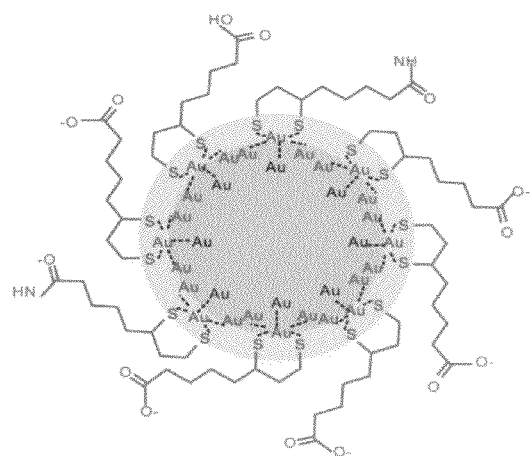
FIG. 1 is a schematic presentation of a gold nanocluster prepared in accordance with one embodiment of the present disclosure.

The detailed description provided below is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

For convenience, certain terms employed in the specification, examples and appended claims are collected here. Unless defined otherwise, all technical and scientific terms used herein have the same meaning as commonly understood by one of the ordinary skill in the art to which the present disclosure belongs.

The singular forms "a", "an", and "the" are used herein to include plural referents unless the context clearly dictates otherwise.

As used herein, the term "about" generally means within 10%, 5%, 1%, or 0.5% of a given value or range. Alternatively, the term "about" means within an acceptable standard error of the mean, when considered by one of ordinary skill in the art.

As used herein, a "pharmaceutically acceptable" component is one that is suitable for use with humans and/or animals without adverse side effects (such as toxicity, irritation and/or allergic response) commensurate with a reasonable benefit/risk ratio.

The term "an effective amount" as used herein refers to the quantity of the gold nanoclusters which is sufficient to yield a desired response. For in vitro application, such as ameliorating oxidative stress and/or aging of a cultured cell, the specific effective amount will vary with factors such as the type of cells that comes into contact with the gold nanoclusters, or the number of passages that the cells have been through. Effective amount may be expressed, for example, as the concentration of the gold nanoclusters being applied, the total mass of the gold nanoclusters (e.g., in grams, milligrams or micrograms), a ratio of the total mass of the gold nanoclusters to the total volume of the cultured medium (e.g., milligrams/ml). Preferably, the gold nanoclusters are applied in a concentration of about 1 to 1,000 nM; more preferably from about 10 to 300 nM; and even more preferably from about 30 to 100 nM. For in vivo application, such as ameliorating oxidative stress and/or aging of a subject, the specific effective amount will vary with factors such as the particular condition being treated, the physical condition of the subject (e.g., the subject's body mass, age, or gender), the type of mammal or animal being treated, the duration of the treatment, the nature of concurrent therapy (if any), and the specific formulations employed. Effective amount may be expressed, for example, as the total mass of the gold nanoclusters (e.g., in grams, milligrams or micrograms), a ratio of the mass of the gold nanoclusters to body mass, e.g., as minigrams per kilogram (mg/kg).

The term "excipient" as used herein means any inert substance (such as a powder or liquid) that forms a vehicle/carrier for the gold nanoclusters. The excipient is generally safe, non-toxic, and in a broad sense, may also include any known substance in the pharmaceutical industry useful for preparing pharmaceutical compositions such as, fillers, diluents, agglutinants, binders, lubricating agents, glidants, stabilizer, colorants, wetting agents, disintegrants, and etc.

The term "vascular factor" or "vascular disease" as used herein refers to any factor or disease effecting the vascular system, including the heart and blood vessels. A vascular factor or disease includes any factor or disease characterized in vascular dysfunction, including, for example, inflammation, intravascular stenosis (narrowing) or occlusion (blockage). Examples of vascular disease include, without limitation, atherosclerosis, coronary artery disease (CAD), myocardial infraction (MI), ischemia, stroke, peripheral vascular disease, and pulmonary vascular disease.

The practices of this invention are hereinafter described in detail with respect to the use of gold nonoclusters in the manufacture of an agent or a medicament for ameliorating oxidative stress and/or aging of a cultured cell or a subject having the oxidative stress and/or aging condition mediated by a vascular disease.

The gold nonoclusters used in the present disclosure are red-emitting gold nanoclusters; specifically, the dihydrolipoic acid (DHLA) coated gold nanoclusters. The DHLA coated gold nanoclusters used in the present disclosure are known to the skilled practitioner as well as the process for their production (Lin et al., 2009 ACS Nano 3:395-401); hence no further explanations are necessary with respect to their preparation. The DHLA coated gold nanoclusters have a fluorescent emission at 650 nm under an excitation wavelength at approximately 420 nm, hence will emit wavelength ranged from red to near infrared. Each gold nanocluster has a particle size ranging from 0.1 to 20 nm, more preferably from 1 to 15 nm, and even more preferably from 2 to 13 nm. The dimension discussed above related to the gold nanoparticle of the present disclosure is in dried state, however, it is of advantage if the gold nanocluster used in the present disclosure is water-soluble or at least dispersible in aqueous medium and/or water; the hydrodynamic size of the dried nanocluster can be significantly larger than the dried size due to the coupling of surrounding solvent molecule such as water. In one specific embodiment example, the gold nanocluster has a hydrodynamic size corresponds to 1 to 30 kDa polyethylene glycol (PEG).

According to one specific embodiment, the gold nanoclusters of the present disclosure have anti-oxidative and/or anti-aging activity when come into contact with cultured cells. In this embodiment, cultured cells were brought into contact with the gold nanoclusters by adding the gold nanoculsters in a concentration from about 1 to 1,000 nM into the culture medium for a period of time, such as from 1 to 10 hours, more preferably from 3 to 7 hours, and even more preferably from 4 to 6 hours, then the spent medium was replaced by a fresh one. The gold nanoclusters treated cultured cells were capable of maintaining their morphology for at least 7 days, more preferably for 14 days, even more preferably for 21 days, and most preferably for 28 days. Cells suitable for treatment with the gold nanoclusters of the present disclosure include, but are not limited to human arotic endothelial cell (HAEC), human epithelial cells, human endothelial progenitor cell (HEPC), human embryonic stem cell, and human mesenchymal stem cell.

In another aspect, the gold nanoclusters of the present disclosure may be used to prepare a pharmaceutical composition or a medicament for treating an oxidative stress and/or aging condition of a subject. The pharmaceutical composition or said medicament comprises an effective amount of the gold nanoclusters of the present disclosure; and a pharmaceutically acceptable excipient. Suitable subject for receiving the pharmaceutical composition or said medicament is the one having oxidative stress and/or aging that is mediated by a vascular factor, which includes but is not limited to, atherosclerosis, inflammation, peripheral vascular disease (PVD), pulmonary vascular disease or coronary artery disease. The subject may be human or mammal such as monkey or chimpanzee.

The pharmaceutical composition or said medicament may be administered systematically or locally. Any customary forms of administration are suitable for administering the gold nanoclusters of the present disclosure. Administration may be carried out, for example, orally, lingually, sublingually, buccally, rectally or parenterally (i.e., by circumventing by the intestinal tract, i.e., intravenously, intraarterially, intracardially, intracutaneously, subcutaneously, transdermally, intraperitoneally or intramuscularly), with oral or intravenous administration being particularly suitable.

For application of the present invention, the gold nanoclusters of the present disclosure are manufactured into usual formulations such as tablets, sugar-coated tablets, pills, granules, aerosols, syrups, emulsions, suspensions, solutions, ointments, creams or gels or any kind, in particular by using inert, essentially nontoxic, pharmaceutically suitable carriers or solvents. To this end, the gold nanoclusters of the present disclosure may be present in each case at a therapeutically effective amount, in particularly at concentrations from about 0.001 to about 99% by weight, preferably from about 0.01 to about 95% weight, of the total mixture, i.e., in amounts sufficient to achieve the indicated or desired dosage range. Nevertheless, it may be necessary, where appropriate, to deviate from the above-indicated amount, depending on the body weight and/or the type of route of administration, on the individual reaction to the medicament, on the type of formulation and/or on the time or interval of administration. Thus, it may be sufficient, in some cases, to manage with less than the above-indicated amount, while in other cases the upper limit mentioned has to be exceeded. In the case of administering relatively large amounts, it may be recommended to distribute said amounts in the form of several single doses over a defined period of time, for example, during a day.

The formulation is prepared, for example, by diluting the gold nanoclusters of the present disclosure with solvents and/or carriers, where appropriate by using emulsions and/or dispersants, it being possible, for example in the case of utilizing water as a diluent, to use, where appropriate, organic solvents as auxiliary solvent.

Depending on the type of administration, it is advantageous to administer the gold nanoclusters of the present disclosure in amounts of from about 0.001 to about 500 mg/Kg of body weight, in particular from about 0.001 to 100 mg/Kg body weight, preferably from about 0.01 to 50 mg/Kg body weight, in order to achieve the desired result. Nevertheless, it may be necessary, where appropriate, to deviate from the above-indicated amount, depending on the body weight and/or the type of route of administration, on the individual reaction to the medicament, on the type of formulation and/or on the time or interval of administration. Thus, it may be sufficient, in some cases, to manage with less than the above-indicated amount, while in other cases the upper limit mentioned has to be exceeded. In the case of administering relatively large amounts, it may be recommended to distribute said amounts in the form of several single doses over a defined period of time, for example, during a day, that is, for example, in the form of several single dose or continuous administration (e.g., continuous infusion). The application in a chronic therapy (e.g., in tablet forms) is likewise possible.

The following Examples are provided to elucidate certain aspects of the present invention and to aid those of skilled in the art in practicing this invention. These Examples are in no way to be considered to limit the scope of the invention in any manner. Without further elaboration, it is believed that one skilled in the art can, based on the description herein, utilize the present invention to its fullest extent. All publications cited herein are hereby incorporated by reference in their entirety.

EXAMPLES

Example 1

Preparation of Gold Nonoclusters

Fluorescent gold nanoclusters used in this study were prepared as previously described (Lin et al., ACS Nano 2009 3:395-401). Briefly, 6-nm gold nanoparticles stabilized with didodecyldimethylammonium bromide (AuNP@DDAB) were synthesized via an established single-phase reaction (Jana and Peng, J Am Chem Soc 2003 125:14280-14281). The composition of AuNP@DDAB is schematically depicted in FIG. 1. Subsequent further dropwise addition of gold precursor solution (AuCl$_3$ in DDAB-toluene solution) caused a gradual loss of plasmon absorption until the solution turned yellowish transparent. Ligand exchange was performed by adding the as-prepared nanoclusters to the reduced lipoic acid (DHLA, dihydrolipoic acid), which was freshly reduced by tetrabutylammonium borohydride (TBAB) with a molar ratio of lipoic acid to TBAB=4:1. This leads to dark-brown nanocluster agglomerates in the resulting mixture and additional UV lamp exposure (365nm, 30 mins) is treated to condense the agglomerates. After discarding the supernatant, nanoclusters re-dispersed in methanol and precipitated again in additional chloroform to remove free surfactants. The dried nanoclusters precipitate could be dispersed in borate buffer (pH 9). Further purification was achieved by three runs of ultracentrifugation (110,000 rpm) to remove excess DHLA. Gold nanoclusters was collected and PBS buffer was changed through a centrifuge filter of 30 kDa molecular weight cut-off (MWCO), leading to a colloidally stable transparent solution of NCs without plasmon peak. The concentration of gold nanoclusters were measured by the extinction coefficient of about 450,000 $M^{-1}cm^{-1}$ at 420 nm.

Example 2

Reduction of Reactive Oxygen Species (ROS) in Cultured Cells 2.1 Cell Culture and Delivery of Gold Nanoclusters of Example 1

Human aortic endothelial cells (HAEC) were maintained in endothelial growth medium MV (the medium is termed "complete culture medium" hereinafter, and all medium were purchased from PromoCell, Heidelberg, Germany). Cells were seeded onto 1% gelatin-coated plastic ware or 2% gelatin-coated glass coverslips in a density of 10,000 cells/cm$^2$ and maintained at 37° C. in a humidified incubator with 95% air and 5% $CO_2$ atmosphere. Chemically synthesized gold nanoclusters of Example 1 were delivered to HAEC using complete culture medium and serum free medium in the absence or presence of cationic lipid reagent (LipofectAMINE 2000, Invitrogen, Carlsbad, Calif., USA). Briefly, the gold nanoclusters of Example 1 and lipid carrier were separately diluted in 250 µl medium without serum and antibiotics. After 5 min incubation, the diluted gold nanoclusters of Example 1 and lipid carrier were gently mixed and incubated for 10 min. The gold nanoparticles/lipid carrier complexes were further added to plastic ware containing cells and conditioned medium (i.e., culture medium in which feeder cells have been cultivated therein for at least 3 to 5 days). After 4 hours of treatment, the medium containing gold nanoclusters of Example 1 was replaced by fresh culture medium, then the cultured HAEC cells were subject to periodic microscopy observation for morphological changes of and flowcytometry analysis of reactive oxygen species (ROS). All samples were examined by a microscope (DM IRBE, Leica, Wetzlar, Germany) with a 20× objective/0.4 aperture and the images were captured by a CCD camera (DC 300F, Leica) at room temperature. Results were depicted in FIG. 2.

Figure 2:
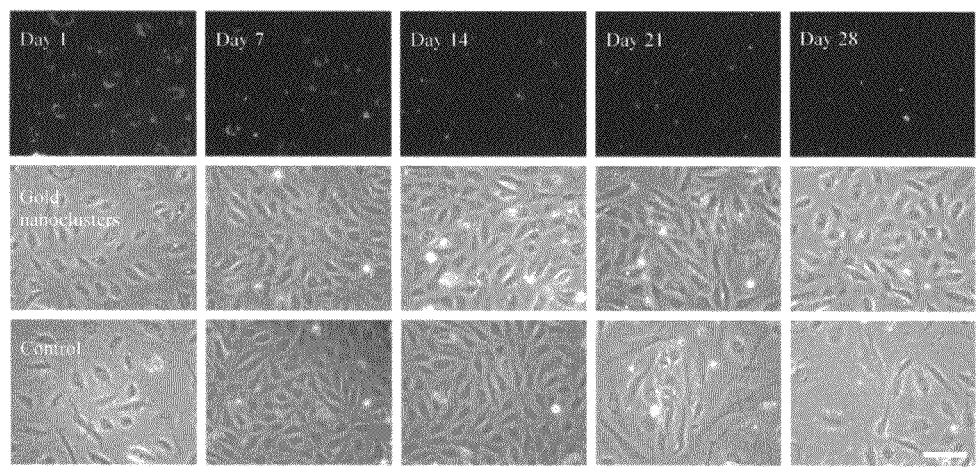
FIG. 2 are photographs of HAECs treated with the gold nanoclusters of Example 1 taken on days 1, 7, 14, 21 and 28, respectively by phase-contrast and fluorescence microscope in accordance with one embodiment of the present disclosure.

FIG. 2 are photographs of HAEC treated with or without the gold nanoclusters of Example 1 respectively taken on days 1, 7, 21 and 28 using a phase-contrast or fluorescent microscope. It is evident from the photographs that the gold nanoclusters of Example 1 are capable of maintaining the morphology of HAEC for at least 28 days in culture.

2.2 Reduction of Reactive Oxygen Species (ROS) by Gold Nanoclusters of Example 1

The ROS levels in HAECs were evaluated using 2, 7-dichlorodihydrofluorescein diacetate dye (DCFDA) (purchased from Invitrogen, Grand Island, N.Y., USA) to reflect the oxidative stress in the cells. This reduced dye was added to cells at a final concentration of 10 µM. After incubation of one hour, cells were washed with HBSS, re-suspended by trypsinization and analysed immediately using a FACScan flow cytometer. The signal of dichlorofluorescein (DCF), an oxidized form of DCFDA, was measured on the FL1 detector and relative intracellular oxidant capacity was estimated using the median fluorescence intensity of the population. Results are summarized in Table 1.

TABLE 1

Attenuation of Reactive Oxygen Species
in HEACs By Gold Nanoclusters

| | Gold signal | | | DCFDA Signal | | |
|---|---|---|---|---|---|---|
| | Intensity | | | Intensity | | |
| | Control (a) | Treatment (b) | (b)/(a) (Fold) | Control (a) | Treatment (b) | (b)/(a) (Fold) |
| 14 day | 1.83 | 17.47 | 9.54 | L 80.22 | 70.52 | 0.88 |
| 21 day | 2.43 | 11.79 | 4.85 | L 150.9 | 111.18 | 0.74 |
| 28 day | 2.83 | 11.89 | 4.20 | C 80.96 | 55.99 | 0.69 |

It is evident from Table 1 that gold nanoclusters of Example 1 are effective in down-regulating the level of ROS or ameilorating oxidative stress for 12%, 26%, and 31% on day 14, 21, and 28, respectively (shown in bold).

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of the present disclosure.

What is claimed is:

1. A method of ameliorating oxidative stress and/or aging of a cultured cell comprising contacting the cultured cell with about 1 to 1,000 nM of a dihydrolipoic acid (DHLA) coated gold nanocluster having a particle size ranging from about 0.1 to 20 nm, wherein,
   the DHLA coated gold nanocluster consists of a gold nanocluster formed by a plurality of gold nanoparticles, and a plurality of DHLAs coated on the gold nanocluster; and the cultured cell is selected from the group consisting of human aortic endothelial cell (HAEC), human epithelial cell, and human endothelial progenitor cell (HEPC).

2. A method of ameliorating a vascular disease mediated oxidative stress and/or aging of a subject, comprising administrating to the subject an effective amount of a dihydrolipoic acid (DHLA) coated gold nanocluster having a particle size ranging from 0.1 to 20 nm, wherein,
   the DHLA coated gold nanocluster consists of a gold nanocluster formed by a plurality of gold nanoparticles, and a plurality of DHLAs coated on the gold nanocluster; and
   the vascular disease is selected from the group consisting of atherosclerosis, coronary artery disease (CAD), myocardial infraction (MI), ischemia, stroke, peripheral vascular disease, and pulmonary vascular disease.

* * * * *